(12) United States Patent
Olivier et al.

(10) Patent No.: US 11,434,465 B2
(45) Date of Patent: Sep. 6, 2022

(54) SYSTEM AND APPARATUS FOR DISCHARGING STERILE MEDIA

(71) Applicant: Merck Patent GmbH, Darmstadt (DE)

(72) Inventors: Stephane Olivier, Rosheim (FR); Gaetan Bour, Ostwald (FR)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/477,926

(22) PCT Filed: Jan. 15, 2018

(86) PCT No.: PCT/EP2018/050808
§ 371 (c)(1),
(2) Date: Jul. 15, 2019

(87) PCT Pub. No.: WO2018/130674
PCT Pub. Date: Jul. 19, 2018

(65) Prior Publication Data
US 2019/0367864 A1     Dec. 5, 2019

(30) Foreign Application Priority Data

Jan. 16, 2017 (EP) ..................... 17290003

(51) Int. Cl.
*C12M 1/00* (2006.01)
*C12M 1/12* (2006.01)
(Continued)

(52) U.S. Cl.
CPC ............. *C12M 99/00* (2013.01); *B01F 25/31* (2022.01); *C12M 37/02* (2013.01);
(Continued)

(58) Field of Classification Search
CPC ...... C12M 99/00; C12M 37/02; C12M 37/00; B01F 5/0403; B01F 2005/0005; B01F 2005/0088; B01F 2215/0073
See application file for complete search history.

(56) References Cited

U.S. PATENT DOCUMENTS 4,090,848 A   5/1978   Naono
5,069,370 A   12/1991  Cady et al.
(Continued)

FOREIGN PATENT DOCUMENTS

EP    0447256 A2    9/1991
JP    S51108887 A   9/1976
(Continued)

OTHER PUBLICATIONS

International Search Report WO2018-130674 dated Aug. 17, 2018 (pp. 1-7).
(Continued)

*Primary Examiner* — Donnell A Long
(74) *Attorney, Agent, or Firm* — Millen, White, Zelano & Branigan, PC; Ryan Pool (57) ABSTRACT

The invention relates to a tubing device for sterile media including a container for storing sterile media, a discharge port for discharging liquid sterile media, an inlet port for introducing fluid into the tubing device and a multiple-way-connector. The multiple-way-connector is connected to the container, the discharge port, the inlet port, and an apparatus for preparing, mixing and discharging a sterile medium for use with a tubing device, including a water inlet port for introducing water, a water outlet port configured to be connected to the inlet port of the tubing device, a fluid pump for conveying the fluid, the fluid pump is connected to the fluid inlet port and the water outlet port and a container support for supporting the container of the tubing device.

15 Claims, 4 Drawing Sheets

(51) Int. Cl.
  *B01F 5/04*    (2006.01)
  *B01F 25/31*   (2022.01)
  *B01F 25/00*       (2022.01)
  *B01F 101/44*      (2022.01)

(52) U.S. Cl.
  CPC ..... *B01F 2025/911* (2022.01); *B01F 2025/93* (2022.01); *B01F 2101/44* (2022.01)

(56) References Cited

U.S. PATENT DOCUMENTS

| | | |
|---|---|---|
| 5,350,080 A | 9/1994 | Brown et al. |
| 5,470,151 A | 11/1995 | Walthall |
| 9,682,353 B2 | 6/2017 | Goodwin et al. |
| 10,328,404 B2 | 6/2019 | Goodwin et al. |
| 10,640,741 B2 | 5/2020 | Kunas et al. |
| 2002/0011496 A1 | 1/2002 | Inaba et al. |
| 2013/0102071 A1 | 4/2013 | Pan et al. |
| 2014/0103077 A1 | 4/2014 | Zumbrum |
| 2014/0231010 A1* | 8/2014 | Park ............... H01L 21/67075 156/345.11 |
| 2015/0273513 A1* | 10/2015 | Buckalter ............ A47K 5/1217 222/146.2 |
| 2016/0128350 A1* | 5/2016 | Rubin ................. B67D 3/0022 222/146.2 |
| 2017/0253847 A1 | 9/2017 | Koseki et al. |
| 2017/0354941 A1* | 12/2017 | Brown .................... B01F 5/008 |

FOREIGN PATENT DOCUMENTS

| | | |
|---|---|---|
| JP | S61193800 U | 12/1986 |
| JP | 06508551 A | 9/1994 |
| JP | 11266853 A2 | 10/1999 |
| JP | 2009034603 A | 2/2009 |
| WO | 9427645 A1 | 12/1994 |
| WO | 06116067 A1 | 11/2006 |
| WO | 13056469 A1 | 4/2013 |
| WO | 2016042741 A1 | 3/2016 |

OTHER PUBLICATIONS

Examination report in corresponding Indian Application 201937032879 dated Jan. 5, 2022 (pp. 1-5).
Office Action dated Nov. 9, 2021 in the corresponding Japanese 2019-538175 Examination Procedure (pp. 1-2).
Search Report in corresponding Brazil application BR112019014291-6 dated May 9, 2022 (pp. 1-4).

* cited by examiner

SYSTEM AND APPARATUS FOR DISCHARGING STERILE MEDIA

FIELD OF INVENTION

The invention relates to a system and an apparatus for mixing, diluting and discharging sterile media and to a method for using such a system.

PRIOR ART

Generally, there are several methods for a sterile medium to be prepared and discharged into respective bags or containers. There are for example large dry bags which can contain up to 20 liters capacity and are prefilled with dehydrated media which can be reconstituted with 20 liters of RO/deionized water flowing through a sterilization filter. For this, the deionized water will be introduced into the bag via a standard connector. The media in the bag will then be mixed with the water to a predetermined concentration corresponding to the working concentration. The mixing is for example done by kneading the water filled media bag until all the dehydrated medium is dissolved.

Another possibility is a media preparator in which powdered media are mixed in a stainless steel vessel. The preparator also sterilizes the mixed media with heat and cools it down afterwards. However, this media preparator is a big apparatus that cannot be used flexibly in different locations and furthermore requires constant maintenance and cleaning. Moreover the media preparator does not allow quick and easy change of media formulation, needing to discard the remaining media, cleaning, refilling, re-sterilizing steps, or using a second preparator to have two media available.

However, all these methods require several steps for mixing and preparing the sterile medium in the respective bag or container. Moreover, all these bags for the sterile media will be filled with water until the correct concentration of sterile medium is reached. This means that the bag with the sterile media will be very heavy since it will initially contain all sterile media, with up to 30 kg or even more. Keeping these bags sterile is also cumbersome, since the discharge tubes are usually directly connecting the discharge port with the bag and cannot be flushed with water while connected.

In addition, in some cases during the tests the transfer of high media volumes in a minimal time is needed. In such case high flow pumps or prefilled bottles are typically used.

DISCLOSURE OF INVENTION

An object of the invention is to provide a closed system for preparing, mixing, diluting and discharging sterile media while reducing the weight, the preparation time and the costs for the system, avoiding the need of a dedicated media kitchen. This is achieved by providing such a system in the form of an apparatus and a tubing device which is preferably disposable. The apparatus and the tubing device are two elements which are interacting with each other to provide the above mentioned system. In use, the apparatus will be used in long-term, while the tubing will usually be replaced for every new batch of sterile media.

The above object is achieved by a tubing device according to claim 1, an apparatus according to claim 8, as well as by a method according to claim 14.

A tubing device for sterile media according to the invention comprises a container for storing sterile media, a discharge port for discharging liquid sterile media, an inlet port for introducing a fluid into the tubing device and a multiple way connector, wherein the multiple way connector is connected to the container, the discharge port and the inlet port by means of a tubing. In this invention, a tubing is for example a tube, pipe, hose or sleeve through which the sterile medium can flow and can be made of different material like plastics or even metal. The container for storing the sterile medium is preferably a bag and the sterile medium is at least in part dehydrated medium stored in the container, preferably completely dehydrated. It is possible to have a premixed sterile medium with a high concentration, above the working concentration. The tubing device is the disposable part of the system for preparing, mixing, diluting and discharging the sterile medium. It is possible that different elements of the tubing device have a different life cycle so the single elements might be replaced at different times as explained later in the application.

Preferably, the multiple way connector is a valve or a pump. The multiple way connector is preferably a three-way connector. Such a multi way connector formed as a valve or a pump is able to control the flow of the fluid in the tubing device by either blocking or opening single ways or by adjusting the direction of the flow.

Furthermore, the tubing device can comprise a one-way valve that is disposed between the inlet port and the multiple way connector. In this way, it can be avoided that a fluid that enters the tubing device is flowing back out of the inlet port.

The tubing device preferably further comprises a filtration device for filtering the fluid that is introduced via the inlet port, the filtration device is disposed between the inlet port and the multiple way connector and preferably between the inlet port and the one way valve. The filtration device ensures that the fluid that is mixed with the sterile medium does not comprise any elements which would deteriorate the quality of the sterile medium.

Furthermore, the filtration device may comprise an airing vent for purging the filtration device from fluid and gas bubbles. Thus, the filtration device can be dried between the uses and the longevity of the filtration device will be increased.

The tubing device with a filtration device can further comprise a plurality of tubings which are disposed between the filtration device and the multiple way connector, the tubings comprise an openable locking device, in particular male and female breakable luers, and a crimping sleeve, respectively, and preferably also a cap at the end of each tubing. Instead of a breakable luer the openable locking device may also be a standard connector or an aseptic connector for pharma application. In a preferred embodiment, male and female breakable luers are used. In this way, the filtration device with the multiple tubings can be used longer and more times than the rest of the tubing device (i.e. the multiple-way connector, the container, etc), since the single tubings will be opened and connected to the rest of the tubing for use, and after use the crimping sleeve will be crimped and clamped together so that the respective tubing is shut off and can be cut off at the crimping sleeve. Then, another tubing of the plurality of tubings will be connected to the rest of the tubing device. Thus, the filtration device does not have to be replaced equally often as the rest of the tubing device.

In another embodiment the discharge port of the tubing device is connected to the inlet port of a buffer reservoir, e.g. a buffer bag, having an inlet port and an outlet port.

The presence of a buffer reservoir allows to provide very large volumes of media that can be dispensed on demand in a very short time during the test.

Another aspect of the invention is an apparatus for preparing, mixing and discharging a sterile medium for use with a tubing device, comprising a fluid inlet port for introducing a fluid, a fluid outlet port configured to be connected to the inlet port of the tubing device, a fluid pump which is preferably a peristaltic pump, for conveying the fluid from the fluid inlet port to the fluid outlet port via a tubing and a container support for supporting the container of the tubing device. The container support can for example be a tray to support the bag, or a hook for hooking it into an eye of the container. This apparatus enables the use of the tubing device as described above. The tubing device and the apparatus provide a system for mixing, preparing, diluting and discharging the sterile medium with the functions as described later.

The apparatus can further comprise a second pump for conveying fluids in the tubing device. This is necessary if the tubing device does not contain a pump itself.

The apparatus may further comprise a heater for heating a fluid introduced in the fluid inlet port. The heating is carried out at a temperature of 30 to 50° C., preferably 35 to 45° C. and most preferably 40° C. The heater is preferably disposed between the fluid pump and the outlet port. Heating the fluid enables a better reaction in the container for the sterile media, i.e. preparing and mixing of the sterile media is carried out easier with heated fluid, in particular in the range that is mentioned above. The heater can either be a flow through heater which is in direct contact with the introduced fluid or a surrounding heater that surrounds the tubing in which the fluid is flowing. A flow through heater is more efficient, but a surrounding heater is better in view of hygiene.

The apparatus can further comprise an actuator for actuating the multiple way connector of the tubing device. This actuator can be a rotary device, but can also be a linear electromagnetic valve actuator for controlling the passage ways of the multiple way connector.

In a further embodiment, when the discharge port of the tubing device is connected to a buffer reservoir, the apparatus may comprise a further transfer pump that works independently from the fluid pump and/or the media pump and is used to dispense the fluid extracted from the buffer reservoir through its outlet port. This pump can be part of an external instrument, i.e. the pumping system of the buffer reservoir may be independent of the other pumping system(s). Alternatively, the fluid transfer pump of the buffer reservoir may be part of one integrated system comprising also the other pump(s).

The apparatus may further comprise a system to monitor the fluid volume inside the buffer reservoir using a weighing system, a liquid level sensor or any other solution known by a person skilled the art for such purpose.

Another aspect of the invention is a method for preparing, mixing and discharging a sterile medium by use of the above mentioned device and apparatus, comprising the steps of providing an exclusive connection between the inlet port of the tubing device and the container of the tubing device, pumping fluid from the fluid inlet port via the fluid outlet port and the multiple way connector to the container of the tubing device, preparing the sterile medium in the container in a predetermined concentration, providing a connection between the container and the discharge port of the tubing device and extracting the prepared medium from the container and discharging it from the discharge port.

The method can further comprise the step of heating the fluid to a predetermined temperature. Furthermore, the method may also comprise the step of diluting the sterile medium by maintaining the connection of the fluid inlet port to the container during discharging of the sterile medium and pumping fluid into the multiple way connector. In this way, it is not necessary to provide the sterile medium in a concentration in that it should be discharged, but it is enough to prepare it to be capable of flowing through the tubing device. By adding further fluid during the discharging action, the sterile medium is further diluted in the multiple way connector to the predetermined concentration in which the sterile medium is to be discharged. Alternatively, sterile medium and sterile fluid can be alternatively pumped through the multiple way connector and discharged in the final container to reach the predetermined concentration after mixing.

The diluting of the sterile medium can be carried out with preheated fluid, so as to enable the discharge sterile medium to be at a predetermined temperature, preferably 35 to 45° C. and most preferably 37° C.

In the case when the discharging port of the tubing device is connected to the inlet port of a buffer reservoir, the method may further comprise a step of filling the diluted medium into the buffer reservoir and a step of discharging the diluted medium from the buffer reservoir through its outlet port. In such case the buffer reservoir can be filled continuously up to a maximum volume by using the fluid pump and the media pump of the apparatus. The medium in the buffer reservoir can then be discharged on demand in the desired volume and independently from the diluting activity of the apparatus, through the outlet port of the buffer reservoir, by using the transfer pump of the buffer reservoir. That pump can be part of an external independent dilutor.

DESCRIPTION OF THE PREFERRED EMBODIMENTS

Figure 1:
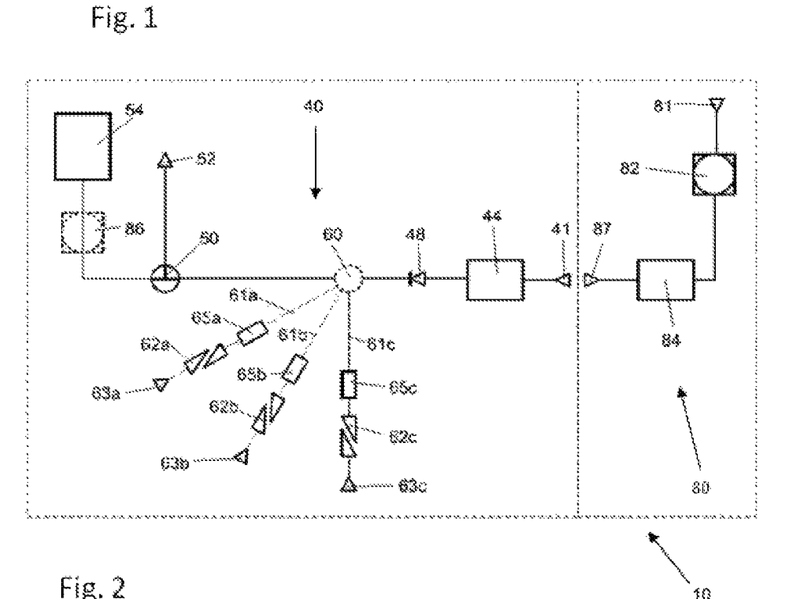
FIG. 1 is a schematic illustration of the system for preparing, mixing, diluting and discharging sterile media.
Figure 7:
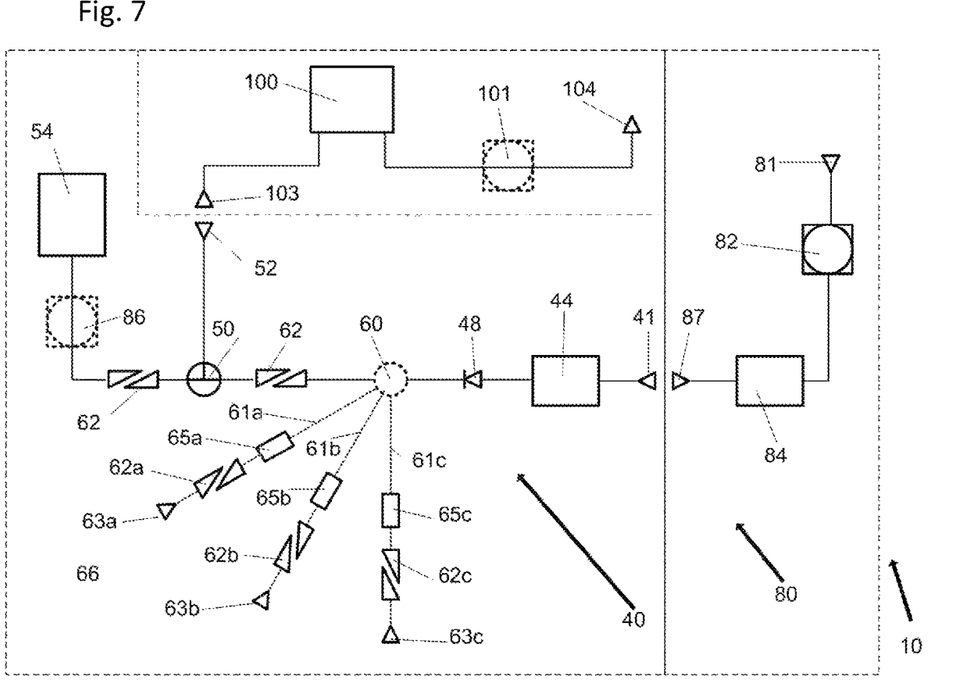
FIG. 7 is a schematic illustration of the system similar to FIG. 1, but further including a buffer reservoir.
Figure 8:
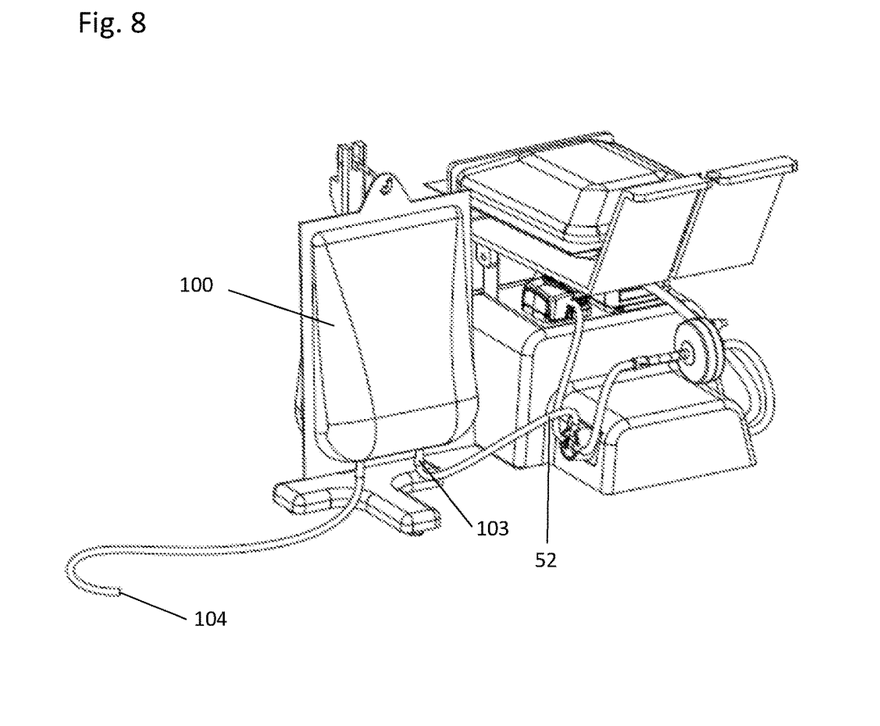
FIG. 8 is a system comprising a combination of the tubing device of FIG. 2 and the apparatus of FIG. 3, wherein the discharging port of the tubing device is connected to a buffer reservoir.

FIG. 1 shows a schematic illustration of a system 10 for preparing, mixing, diluting and discharging sterile media. In FIG. 1 the fluid flow through the single elements of the tubing device 40 and the apparatus 80 is schematically shown. The fluid enters the apparatus 80 at the input port and is conveyed by means of a water pump 82 to a heater 84. The fluid is heated therein and transferred to the tubing device 40. In the tubing device 40, the fluid runs through a filtration device 44 in which it is filtered. From there, the fluid is running through a one-way valve 48 to a multiple way connector 50, here a three-way connector or more preferably a three-way-valve or three-way pump. From the three-way connector 50, only one way leads to the discharge port 52, the other passageway leads to the container 54 that stores the sterile medium. Not all of the elements as shown in FIG. 1 and FIG. 7 have to be present to carry out the invention, but by including these elements, the invention is the most flexible.

In theory, the fluid can be any fluid suitable for being mixed with a powdered or highly concentrated medium in a container. However, in the specification of this application it is named water, in particular de-ionized water or distilled water which are the preferred forms of the fluid used in the invention.

First, the tubing device 40 will be explained. In the tubing device 40, the single elements are connected to each other via tubings, i.e. small sleeves, hoses or tubes. These tubings are preferably made of plastics material. The tubing device 40 comprises a container 54 for sterile media. Usually, this is a bag which is filled with dehydrated culture medium, in particular completely dehydrated medium. Completely dehydrated medium has a very long shelf life and stability. Moreover, the volume of a bag with (completely) dehydrated medium is several factors lower than the total volume of medium that can be delivered at the final working concentration. The dry medium can be buffered peptone water, lactose broth, modified tryptic soy broth or any other medium that requests aseptic or sterile preparation and dispensing conditions. The container 54 is connected via a tubing to the multiple way connector 50. In some applications, the medium stored in the container 54 needs to be completed by further adding additives. In such cases, a septum can be available on the container 54 to allow aseptic transfer using standard syringes or septum systems. To avoid formation of precipitate for some difficult to dissolve media, it is also possible to use compartmented media bags allowing sequential reconstitution. For example the media bag can contain a powdered medium and a pre-dilution buffer in two different compartments within the bag. If the bag is then placed on the apparatus or before it is placed on the apparatus, the seal between the two compartments can be broken and the pre-dilution buffer is mixed with the powdered medium. The prepared medium is then completed with the sterile water and mixed.

Figure 2:
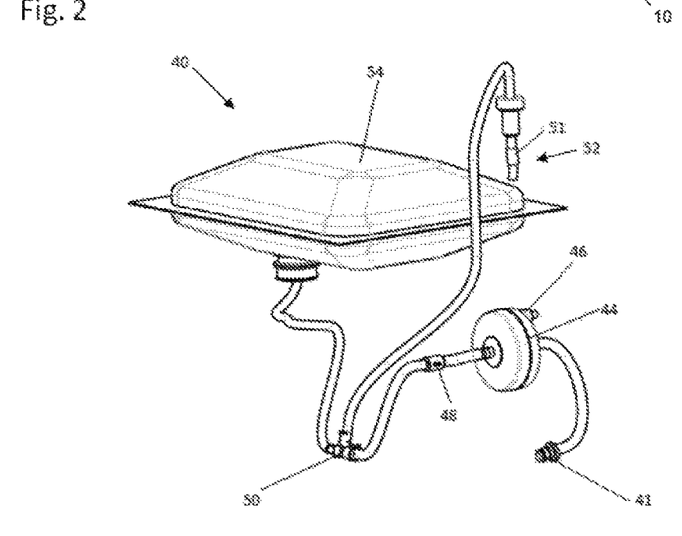
FIG. 2 shows a tubing device according to the invention.
Figure 3:
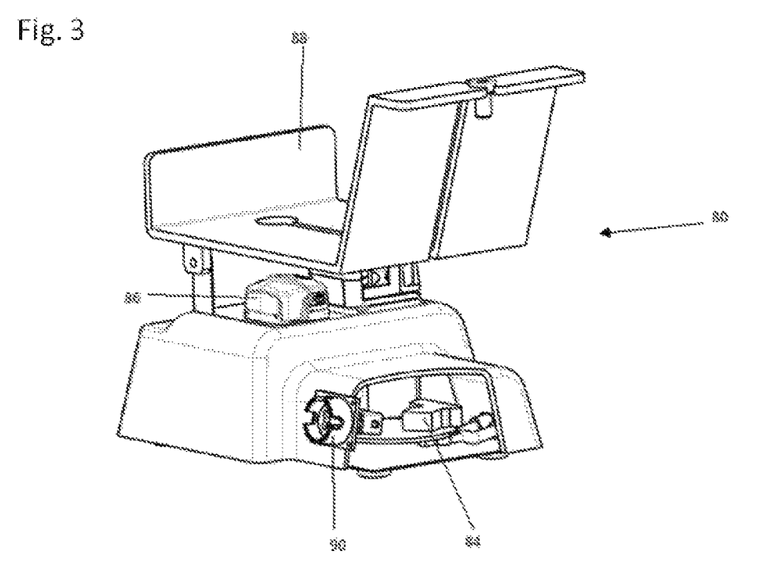
FIG. 3 shows an apparatus according to the invention.
Figure 4:
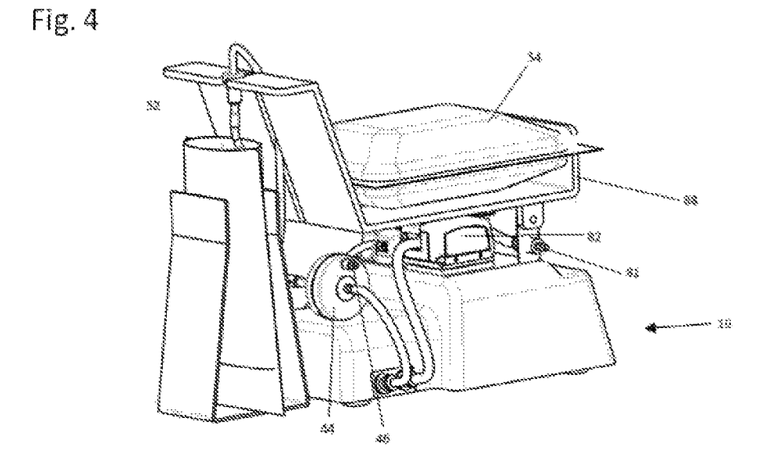
FIG. 4 is a system comprising a combination of the tubing device of FIG. 2 and the apparatus of FIG. 3.

The multiple way connector 50 is in the present embodiments as shown in the figures a three-way connector. However, if there is need, it can also be a four-way or a five-way connector for as many passageways as necessary. The multiple way connector 50 can open and close each passageway in a way that every tubing can be connected with the other tubings. Preferably, each passageway can be closed and opened individually, for example by using a linear electromagnetic valve actuator. This actuator can be part of the tubing device 40, but also can be a part of the apparatus 80 as described later. In the present embodiment, the multiple way connector 50 comprises a lever which can be switched between three positions. As stated above, one passageway leads to the container 54, another passageway leads to the discharge port 52 through which the liquid sterile medium will be discharged in a predetermined concentration, and the third passageway leads to the inlet port 41 for introducing the water into the tubing device 40. In the embodiment shown in the FIGS. 2 to 4, the switch of the three-way connector 50 connects in the first position the tubing to the inlet device 41 with the tubing to the outlet device 52 and the tubing to the container 54 is closed. In the second position of the switch of the three-way connector 50, the inlet port 41 is connected to the container 54, but the tubing to the discharge port 52 is closed. In the third position of the switch of the three-way connector 50, the container 54 is connected to the discharge port 52 and in the fourth position of the switch of the three-way connector 50 all tubings are connected at the three-way connector 50 with each other.

The discharge port 52 for discharging the liquid sterile media is connected via a tubing to the multiple way connector 50 and comprises at the end a closure like a cap or a tip plug. The tubing to the discharge port 52 can also be closed in the tubing, so that one end of the tubing is simply a dead end. For use, the closed end of the outlet tubing is then cleaned and aseptically cut with sterile scissors or the cap or plug is removed to enable discharging of sterile media.

The final passage way of the multiple way connector 50 of the present embodiment leads to the inlet port 41. The inlet port 41 can be covered and closed like the discharge 52 port, but also can have a connector plug that can be plugged into a corresponding connector socket on the discharge port 87 of the apparatus 80. Between the multiple way connector 50 and the inlet port 41 is preferably arranged a one-way valve 48. The one-way valve prevents that liquid flows back from the multiple way connector 50 to the inlet port 41. The one-way valve is arranged between the filtration device 44 and the multiple way connector 50.

Furthermore, the tubing device 40 can comprise a filtration device 44. The filtration device 44 serves to filter the water introduced into the water inlet port 41. The filtration device 44 ensures that only uncontaminated sterile fluid is conveyed into the container 54. The filtration device 44 comprises an airing vent 46 that serves to de-gas the filtration device when the system is not in use.

In one embodiment the filtration device 44 is connected to the multiple way valve 50 through a single aseptic connector 62. This single connector 62 can be used once or can also be used several times to connect the filtration device 44 to the multiple way valve 50, i.e. after use the connector is opened, the container 54 is replaced by a new one which is then connected to the connector 62.

In another embodiment the multiple way valve 50 is connected to the container 54 through a single aseptic connector 62. This single connector 62 can be used once or can also be used several times to connect the multiple way valve 50, i.e. after use the connector is opened, the container 54 is replaced by a new one which is then connected to the connector 62.

Figure 5:
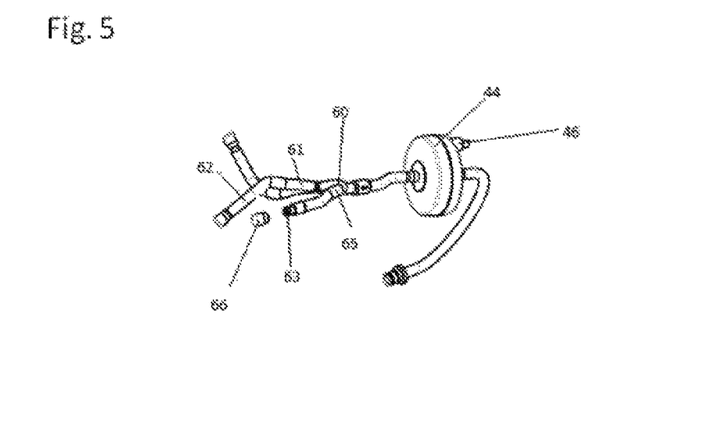
FIG. 5 shows a filtration device for multiple usage.

In a preferred embodiment shown in FIGS. 1 and 5, the filtration device 44 might contain another multiple way connector 60. Each of the tubings leading away from the multiple way connector 60 is configured to be connected with the tubing leading from the multiple way connector 50 for connecting the passageways to the container 54 and the discharge port 52. The different tubings 61a, 61b, 61c comprise breakable (male and female) luers which can be broken to allow fluid flowing through the outlet 63a-c, respectively. Furthermore, in front of the breakable luers is provided a crimping sleeve 65a-c. These crimping sleeves 65a-c serve to close the respective passageway when it has been used and another container 54 is to be connected to the filtration device 44. I.e. although the tubing device 40 is a disposable product, some parts of the tubing device 40 can last longer than others. For this purpose, the filtration device can comprise the above mentioned multiple-way connector 60 with the different passages 61a-c. If one passage is used, the corresponding protective cap 66 is removed and the passage 61 connected to the tubing to the multiple way connector 50. If then the container 54 is emptied, the passage way 61a-c that has been connected to the multiple way connector 50 is closed by clamping the crimping sleeve 65a-c together and another passage way can be connected to another tubing of another tubing device.

Figure 6:
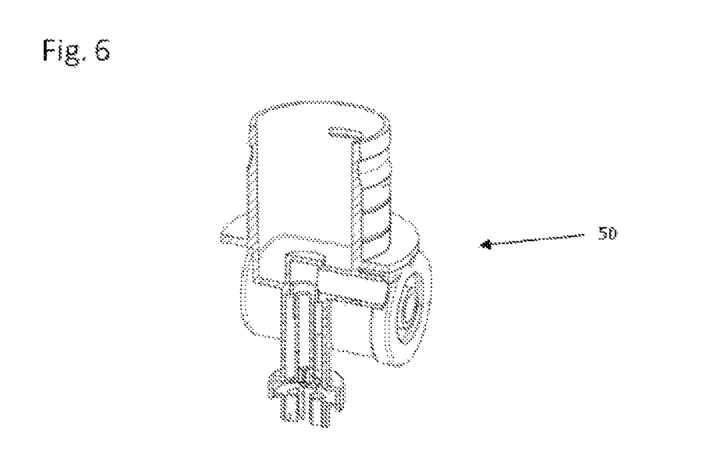
FIG. 6 shows a multiple way connector formed as a 3 way pump.

Furthermore, the multiple-way connector 50 can also be formed as a pump. By doing this, the apparatus 80 as described afterwards does not need a separate pump 86 for conveying the fluids in the tubing device. If the multiple-way connector 50 is formed as a flow-through pump, opening and closing of the different passage ways is managed in the following. In the beginning, the discharge port 52 is closed, either by a plug or by the above mentioned dead end of the discharge port 52 before use. Therefore, the tubing from the multiple-way connector 50 to the discharge port 52 cannot be filled with a fluid. Thus, all the fluid entering the inlet port 41 will eventually flow into the container 54. Afterwards, the rotational direction of the motor of the flow-through pump 50 can be reversed, the discharge port 52 is opened and the passage way to the inlet port 41 will either be blocked by the one-way valve 48, or by fluid that is being pumped into the flow-through pump 50 by the fluid pump 82.

FIG. 7 shows an embodiment in which the discharge port 52 of the tubing device is connected to the inlet port of a buffer reservoir 100, e.g. a buffer bag, having an inlet port 103 and an outlet port 104. In such case the outlet port 104 of the buffer reservoir serves as the discharge port for the system. The presence of a buffer reservoir allows to provide very large volumes of media that can be dispensed on demand in a very short time during the test.

The apparatus 80 mainly comprises a fluid pump or water pump 82 and a container support 88 for supporting the container 54 of the tubing device 40. In the present embodiment shown in FIG. 3 the support 88 is a tray that can accommodate and support a container 54 like a bag. The container support can also be a hook which can be hooked into an corresponding eye comprised by the container. Furthermore, the apparatus 80 comprises an inlet port 81 for introducing the fluid/water and an outlet port 87 which is to be connected to the inlet port 41 of the tubing device 40. The inlet port can be located at or as a part of the fluid pump 82 or can be disposed at the end of a tubing that connects the fluid pump 82 with the inlet port 81. The fluid pump 82 can be a flow-through pump, but preferably it is a surrounding pump like a peristaltic pump in which the tubing can be accommodated. In this way, the tubing can also easily be replaced in the apparatus if necessary. Such fluid pumps are known to the skilled person. Finally, the apparatus 80 comprises an outlet port 87 which can be a part of the fluid pump 82 or the heater 84 or which can be connected to them by means of a tubing. The outlet port 87 is to be connected to the inlet port 41 of the tubing device 40.

The apparatus 80 preferably also comprises a heater 84. The heater 84 serves to heat the water so that the inlet port 81 can also be supplied with cold water and the media in the bag 54 can still be mixed and prepared with warm water. The heater 84 can be either a flow-through heater where the water flows through the heater, but can also be a surrounding heater accommodating the tubing of the apparatus. A flow-through heater can more efficiently heat the water, whereas a surrounding heater is hygienically cleaner, but might need more energy to heat the water.

The inlet port 81 can be connected to a water supply in a laboratory, but can also be connected to a water container that can also be part of the apparatus 80.

To use the system, the tubing device 40 has first to be mounted on the apparatus 80. For this, the apparatus comprises the inlet port 81, the water pump 82, the outlet port 87 and preferably also the heater 84. These elements are connected to each other via tubings. The container 54 is placed on the support 88 for the container 54, for example laid down on the tray or hooked onto the hook, and the inlet port 41 of the tubing device 40 is connected to the outlet port 87 of the apparatus 80. If the tubing device 40 comprises an own pump, the pump is placed onto a corresponding accommodation location on the apparatus 80. Such a pump could be the afore mentioned 3-way-pump that serves simultaneously as the multiple-way connector, but can also be an additional pump located between the container 54 and the multiple-way connector 50. If the tubing device 40 does not comprise a pump, the tubing between the container 54 and the multiple way connector 50 is mounted into a media pump 86 which is also preferably comprised by the apparatus 80. This pump 86 is preferably a peristaltic pump. In case the multiple-way connector 50 is a multiple-way or a three-way valve, the multiple-way connector is linked with a rotary actuator 90 which is preferably provided on the apparatus. If the multiple-way connector is a linear electromagnetic valve, it will be linked to a corresponding actuator/control device on the apparatus. The system 10 for preparing, mixing, diluting and discharging sterile media is then ready for use.

At first, the inlet port 81 of the apparatus 80 will be connected to a fluid supply that is for example a water supply (in the following the term "water" is used to describe the functionality). This can be a water supply in a laboratory or a container with water as mentioned above. The water is preferably pretreated water like de-ionized water. In the following, the use of the system 10 is described with all the elements as mentioned before, including the heater 84, the filtration device 44, a three-way valve 50 as a multiple way connector but not with a multiple-way connector 60 and passageways 61 that has been described above.

At first, the three-way valve is adjusted in position 2 so that the inlet port 41 is connected to the container 54 and the discharge port 52 is still closed and/or sealed. The water enters the system 10 into the inlet port 81. The water pump 82 conveys the water through the tubing of the apparatus 80 and the water flows into the heater 84 and is heated up to a temperature of 30 to 50° C., preferably 35 to 45° C. or essentially 40° C. After that, the heated water flows through the outlet port 87 into the inlet port 41 of the tubing device 40. The water is flowing into the filtration device 44 in which particles, micro-organisms and elements can be filtered from the water to ensure that only sterile water is flowing past the filtration device 44. The water then passes the one-way valve 48 and flows into the three-way valve 50 which is adjusted in the second position so that the water can pass through into the tubing to the container 54. The container 54 is in this example filled with completely dehydrated medium and the water is pumped by means of the media pump 86 into the container 54. The dissolution of the dehydrated medium is highly improved by heated water. The dissolution can be completed with a manual massage, with steering (magnetic bar), by waves which are created by an automated repetitive bag tilting or repetitive and automated local bag compression (similar to a peristaltic blender). In this way, the medium in the container or bag is dissolved into a homogeneous liquid suspension. The medium in the bag is preferably still not dissolved into a concentration determined for the discharge port. Instead, the concentration of the medium in the container is much higher.

The discharge port 52 is then opened by cutting the end or taking off the cap and the three-way valve 50 is switched into position 3 in which all three tubings are connected. Then, the water pump 82 pumps more water into the tubing device while the media pump 86 is reversed and pumps the high concentration medium into the three-way valve 50. The sterile medium is mixed with the water in the three-way valve 50 to the predetermined concentration, flows through the tubing to the discharge port 52 and is discharged.

Before and/or after discharging the sterile medium, the tubings with the exception of the tubing from the multiple way connector 50 to the container 54 can be cleaned. This is done by switching the three-way valve 50 into position 1, in which the discharge port 52 is connected to the inlet port 41, but the tubing to the container 54 is blocked. Then, the preferably hot water can flush the tubings and clean it from media residue.

The concentration of sterile medium can also be adjusted after discharging the diluted medium by further discharging only water, when the three-way valve is in the cleaning arrangement of position 1.

After use, the system 10 for discharging the sterile media can also be temporarily stopped for further use at another time. For this, the tubing is flushed with warm sterile water as described. The flow rate and the temperature are selected for optimal tube cleaning. After that, the discharge port can be crimped with at least one crimping sleeve 51 which can be arranged at the end portion of the discharge device. In this way, the discharge port is aseptically sealed. There can be multiple crimping sleeves 51 and for each use, the discharge port can be cut open again at predetermined locations between the crimp sleeves. The inlet port 41 of the tubing device 40 is then disconnected from the outlet port 87 of the apparatus 80 and the inlet port 41 and the outlet port 87 are closed with a protective plug. Then, the container 54 can be safely stored at the optimal temperature and reused later.

The discharge port can also comprise a multiple-way connector which can be simultaneously connected to different test bags which are then also simultaneously filled when the diluted medium is discharged through the discharge port.

The apparatus 80 can also comprise a weighing platform to determine the volume of medium dispensed through the discharge port 52, according to the sample weight.

When the discharge port 52 of the tubing device 40 is connected to a buffer reservoir 100 as shown in FIG. 8, the apparatus may comprise a further transfer pump 101 that works independently from the fluid pump 82 and/or the media pump 86 and is used to dispense the fluid extracted from the buffer reservoir 100 through its outlet port 104. This pump can be part of an external instrument, i.e. the pumping system of the buffer reservoir may be independent of the other pumping system(s). Alternatively, the fluid transfer pump of the buffer reservoir may be part of one integrated system comprising also the other pump(s). The transfer pump 101 may be a peristaltic pump allowing for transferring a desired amount of the content of the buffer reservoir.

The apparatus 80 can also comprise a pod having a hook that can be used to hold the buffer reservoir 100.

The apparatus may further comprise a system to monitor the fluid volume inside the buffer reservoir using a weighing system, a liquid level sensor or any other solution known by a person skilled the art for such purpose.

During operation of an apparatus with buffer reservoir, the diluted medium is transferred into the buffer reservoir 100 through its inlet port 103 and discharged from the buffer reservoir through its outlet port 104. In one embodiment the buffer reservoir 100 is filled continuously up to a maximum volume by using the fluid pump and the media pump of the apparatus. The medium in the buffer reservoir is discharged on demand in the desired volume and independently from the diluting activity of the apparatus, through the outlet port 104 of the buffer reservoir, by using the transfer pump 101 of the buffer reservoir.

In the following, examples of applications are given.

Application 1 for pathogen testing (*Salmonella, Listeria*, and EHEC for example) in food products by dispensing single strength medium: The system is used for the initial dilution of the food sample before enrichment. 25 g of pre-weighted food sample is diluted 1/10 by the system by adding 225 ml of culture medium pre-heated (or not) (for example BPW, Lactose Broth, mTSB, Half Fraser, bLEB) at the right concentration (e.g. 1×) prepared from the reconstituted concentrated medium stock diluted with sterile filtered water. The diluted food sample is then processed according to the standard procedures known to the skilled persons. For some food products, composite samples of 375 g are diluted 1/10 by adding 3.375 L of medium. For other food products, samples are diluted 1/4, 1/6 with culture medium. Pre-warmed medium, obtained by heating the filtered water, is also required for some applications (for example rapid detection of *Salmonella*).

Application 2 for pathogen testing (*Salmonella, Listeria*, and EHEC for example) in food products by dispensing single strength medium: The system is used for the initial dilution of the food sample before enrichment. The food sample (for example 25 g, 375 g) is weighted and diluted (e.g. 1/10, 1/4, 1/6, 1/20) by the system by adding the corresponding volume of culture medium pre-heated (or not) (BPW, Lactose Broth, mTSB, Half Fraser, bLEB for example) at the right concentration (e.g. 1×) prepared from the reconstituted concentrated medium stock diluted with sterile filtered water. The diluted food sample is then processed according to the standard procedures known to the skilled persons. Pre-warmed medium obtained by heating the filtered water, is also required for some applications (for example rapid detection of *Salmonella*).

Application 3 for water quality testing, by dispensing double strength culture medium: The system is used for the initial dilution of the water sample before enrichment. The water sample is either diluted in 50 ml of 1× concentrated culture medium dispensed by the system (sample <10 ml) or diluted 1/2 with 2× culture medium dispensed by the system (sample>10 ml), as described for example for *Salmonella* (ISO 19250:2010). The diluted sample is then processed according to the standard procedures known to the skilled persons. Testing of some liquid food sample may also require the dilution in double strength culture medium.

Application 4 for dispensing fixed volume of culture medium for environmental monitoring: The system is used to dispense 1× concentrated culture medium (for example 100 ml) from the reconstituted concentrated medium stock diluted with sterile filtered water in a sample bag or equivalent. The test swab or sponge is then placed in the bag and incubated.

Application 5 for pharma sterility testing by direct inoculation of the culture medium according to USP71 and equivalent European and Japanize pharmacopeia: The system is used to aseptically fill individual sterile containers with sterile culture medium by reconstituting and diluting a concentrated stock of sterile medium (TSB or FTM for example) with sterile filtered water (pre heated to facilitate the dissolution). After filtration of the sample (for example filterable liquids, antibiotic liquids, soluble solids, oils and oily solutions, ointments and creams, prefilled syringes, solids for injection, sterile aerosol products, devices with sterile labelled pathways), the filter is aseptically placed in one container prefilled with medium, and the container is incubated at the recommended temperature for the recommended duration (for example 14d at 32.5° C.+/−2.5 for FTM and 14 d at 22.5° C.+/−2.5 for TSB).

Application 6 for Pharma sterility testing according to USP71 and equivalent European and Japanize pharmacopeia. The system is used to aseptically fill individual sterile containers with sterile culture medium by reconstituting and diluting a concentrated stock of sterile medium (TSB or FTM for example) with sterile filtered water (pre heated to facilitate the dissolution). The non-filterable sample (for example catgut, surgical sutures, solids, purified cotton, gauze, surgical dressings, sterile devices, oily liquids, ointments and creams after dilution and neutralization if required), the filter is aseptically placed in one container prefilled with medium, and the container is incubated at the recommended temperature for the recommended duration (for example 14d at 32.5° C.+/−2.5 for FTM and 14 d at 22.5° C.+/−2.5 for TSB). The concentration of the culture medium dispensed by the system can be 1×, or higher concentration if a large volume of diluted sample is to be analyzed).

Application 7 for the same applications as described previously in applications 1 to 6, where the customer wishes to supplement the medium with specific sterile chemicals. The sterile solution is aseptically injected in the bag through the septum. Alternatively, the sterile solution, in a bag or a similar container, can be aseptically connected to the bag through a sterile tubing.

The supplements can be antibiotics or chemicals offering more selectivity, for selective medium for food pathogen testing (for example mTSB supplemented with novobiocin for STEC detection according to ISO16654, mBPW supplemented with pyruvate according to BAM4A for Diarrheagenic *Escherichia coli* detection).

The supplements can also be neutralizers for pharma sterility testing or cosmetics testing to neutralize the antimicrobial agents in the samples.

Application 8: The same application as described previously in applications 1 to 6 where medium is provided as a concentrated liquid solution and not powder to be reconstituted Application 9: The same application as described previously in applications 1 to 6, where the culture medium needs sequential reconstitution to reduce the formation of precipitates.

Application 10: The same application as described previously in applications 1 to 6, where culture medium needs to be delivered at a high flow rate (e.g. over 2 L/min). The system is used to prepare the culture medium and feed a buffer bag. This buffer bag is connected to an additional dispensing pump tubing (e.g. a peristaltic pump or a gravimetric dilutor) for culture medium dispensing in the test container at a flow rate larger than the flow rate of the system. The buffer bag is being refilled by the system continuously. This allows a higher throughput, notably for large sample batches (e.g. 375 g samples to be diluted in 3.375 L) to be processed in a minimal time.

LIST OF REFERENCE NUMBERS system 10
tubing device 40
inlet port of tubing device 41
one way valve 48
filtration device 44
airing vent 46
multiple way connector 50
crimping sleeve 51
discharge port of tubing device 52
container 54
multiple way connector 60
passageways 61 (a-c)
breakable luers 62 (a-c)
outlet connectors 63 (a-c)
crimping sleeves 65 (a-c)
protective cap 66
apparatus 80
inlet port of apparatus 81
fluid pump 82
heater 84
media pump 86
outlet port of apparatus 87
actuator 90
buffer reservoir 100
transfer pump 101
inlet port of buffer reservoir 103
outlet port of the buffer reservoir 104

The invention claimed is:

1. Apparatus (80) for preparing, mixing and discharging a sterile medium for use with a tubing device (40) comprising:
   a container (54) for storing sterile media;
   a discharge port (52) for discharging liquid sterile media;
   an inlet port (41) for introducing water into the tubing device; and
   a multiple-way-connector (50), wherein the multiple-way-connector (50) is connected in parallel to:
      a valve or a pump that is connected by tubing to the container (54),
      the discharge port (52), and
      the inlet port (41),
   wherein the apparatus comprises
   a water inlet port (81) for introducing water;
   a water outlet port (87) configured to be connected to the inlet port (41) of the tubing device (40);
   a fluid pump (82) for conveying the fluid, the fluid pump (82) is connected to the fluid inlet port (81) and the water outlet port (87); and
   a container support (88) for supporting the container (54) of the tubing device (40).

2. The apparatus of claim 1 wherein the tubing device (40) further comprises a one-way valve (48) that is disposed between the inlet port (41) and the multiple-way-connector (50).

3. The apparatus of claim 1 wherein the tubing device (40) further comprises a filtration device (44) for filtering water introduced via the inlet port, the filtration device is disposed between the inlet port (41) and the multiple-way-connector (50).

4. The apparatus of claim 3 wherein the filtration device comprises an airing vent (46).

5. The apparatus of claim 3, wherein a plurality of tubing (61) are disposed between the filtration device (44) and the multiple way connector (50), wherein a tubing comprises an openable locking device (62) and a crimping sleeve (65).

6. The apparatus of claim 1 wherein the tubing device (40) further comprises a buffer reservoir (100) having an inlet port (103) that is connected to the discharge port (52) and an outlet port (104).

7. Apparatus (80) according to claim 1, further comprising a second pump (86) for conveying fluids in the tubing device (40).

8. Apparatus (80) according to claim 1, further comprising a heater (84) for heating fluid introduced in the fluid inlet port (81).

9. Apparatus (80) according to claim 8, wherein the heater (84) is a flow through heater or wherein the heater (84) is surrounding the tubing.

10. Apparatus (80) according to claim 1, further comprising an actuator (90) for actuating the multiple way valve (50).

11. Apparatus (80) according to claim 1, further comprising a transfer pump (101) for conveying fluids from the buffer reservoir (100) to the outlet port (104).

12. Method for preparing, mixing and discharging a sterile medium, by use of an apparatus (80) according to claim 1, and a tubing device (40) for sterile media comprising

- a container (54) for storing sterile media;
- a discharge port (52) for discharging liquid sterile media;
- an inlet port (41) for introducing fluid into the tubing device; and
- a multiple-way-connector (50), wherein the multiple-way-connector (50) is connected to the container (54), the discharge port (52) and the inlet port (41), the method comprising the steps of providing an exclusive connection between the inlet port (41) of the tubing device (40) and the container (54) of the tubing device (40);

pumping fluid from the fluid inlet port (81) via the outlet port (87) and the multiple way connector (50) to the container (54) of the tubing device (40);

preparing the sterile medium in the container (54) at a predetermined concentration;

providing a connection between the container (54) and the discharge port (52) of the tubing device (40);

extracting the prepared medium from the container (54) and discharging it from the discharge port (52).

13. Method according to claim 12, further comprising the step of heating water to a predetermined temperature.

14. Method according to claim 13, wherein a predetermined quantity of diluted medium is discharged at a predetermined temperature.

15. Method according to claim 12, further comprising the step of diluting the sterile medium by maintaining the connection of the fluid inlet port (81) to the container (54) during extraction of the sterile medium and pumping fluid into the multiple way connector (50).

* * * * *